United States Patent [19]
Lehrer

[11] Patent Number: 5,945,289
[45] Date of Patent: Aug. 31, 1999

[54] METHOD FOR DETECTING PROSTATE CANCER BY APOLIPOPROTEIN E (APO-E) GENOTYPING

[76] Inventor: Steven Lehrer, Thirty W. Sixtieth St., New York, N.Y. 10023

[21] Appl. No.: 08/995,083

[22] Filed: Dec. 19, 1997

Related U.S. Application Data

[60] Provisional application No. 60/033,872, Dec. 20, 1996.
[51] Int. Cl.⁶ .............................. C12Q 1/68; C12P 19/34
[52] U.S. Cl. ................................................. 435/6; 435/91.2
[58] Field of Search .............................. 435/6, 91.2, 91.1, 435/7.1

[56] References Cited

PUBLICATIONS

Gerald P. Murphy, et al., Cancer Aug. 15, 1996, vol. 78 (4): 809–818.
Ya–Ting Chen, et al., Adult Urology, 1996, vol. 47 (4): 518–524.
Albert A. Luderer, Ph.D., et al., Adult Urology, 1995, vol. 46 (2): 187–194.
William J. Catalona, M.D., et al., JAMA, Oct. 18, 1995, vol. 274 (15): 1214–1220.
Gerald Murphy, et al, Anticancer Reserach, 1995, vol. 15: 1473–1480.
Mitchell H. Sokoloff, et al., The Jorunal of Urology, 1996, vol. 156: 1560–1566.
M.H. Sokoloff, et al., The Journal of Urology, 1998, vol. 159: 1.
Graham F. Grene, et al., American Journal of Pathology, May 1997, vol. 150 (5): 1572–1582.
Armelle Degeorges, et al., Int. J. Cancer, 1996, vol. 68: 207–214.
A.M. Saunders, et al., *The Lancet*, Jul. 13, 1996, vol. 348: 90–93.
Robert W. Mahley, Science, Apr. 29, 1988, vol. 240: 622–630.
Masaaki Miyata, et al., Nature Genetics, Sep. 1996, vol. 14: 55–61.
Susan J. Duthie, et al., Cancer Research, Mar. 15, 1996, vol. 56: 1291–1295.
E. H. Corder, et al., Science, Aug. 13,1993, vol. 261: 921–923.
Peggy Eastman, et al., News, Journal of the National Cancer Inst., Jul. 17, 1996, vol. 88 (14): 952–953.
Joan Stephnenson, Ph.D., JAMA, Sep. 18, 1996, vol. 276 (11): 861–863.
Angelo M. Scanu, The Lancet, May 11, 1991, vol. 337: 1158–1159.
Judes Poirier, et al., The Lancet, Sep. 18, 1993, vol. 342: 697–699.
Daniel Bouthillier, et al, Journal of LIPID Research, 1983, vol. 24: 1060–1069.
D. Blacker, M.D., et al., Neurology, 1997, vol. 48: 139–147.
David A. Twillie, M.D., et al., Urology, Mar. 1995, vol. 45 (3): 542–549.
William J. Catalona, et al., The Journal of Urology, Dec. 1997, vol. 158: 2162–2167.
Steven Lehrer, et al., Journal Cancer Research Clinical Oncology, 1995, vol. 121: 123–125.
Grant E. Meyer, B.S., et al., Cancer, Dec. 1, 1995, vol. 76 (11): 2304–2311.

*Primary Examiner*—Eggerton A. Campbell
*Attorney, Agent, or Firm*—Dann, Dorfman, Herrell and Skillman

[57] ABSTRACT

Methods for assessing a patient's predisposition for developing prostate cancer are disclosed. PCR assays using primers for apolipoprotein E (ApoE) genotypes and primers for known prostate cancer molecular markers such as PSA are applied to biological samples. ApoE4/E4 homozygosity coupled with elevated PSA or other prostate cancer marker levels in the blood, indicate the likelihood that prostate cancer is present.

7 Claims, No Drawings

METHOD FOR DETECTING PROSTATE CANCER BY APOLIPOPROTEIN E (APO-E) GENOTYPING

This application claims priority under 35 U.S.C. §119(e) to U.S. Provisional Application 60/033,872 filed Dec. 20, 1996, the disclosure of which is incorporated herein by reference.

FIELD OF THE INVENTION

This invention relates to the field of cancer detection and diagnosis. More specifically, the invention provides methods for detecting the presence of or predisposition to prostate cancer utilizing ApoE genotyping in conjunction with additional prostate cancer screening assays.

BACKGROUND OF THE INVENTION

Several publications are referenced in this application by numerals in parentheses in order to more fully describe the state of the art to which this invention pertains. Full citations for these references are found at the end of the specification. The disclosure of each of these publications is incorporated by reference herein.

This year prostate cancer is expected to be diagnosed in 200,000 men in the U.S. and to result in the loss of 38,000 lives. Such numbers make prostate cancer the most frequently diagnosed malignancy (other than that of the skin) in American males and the second leading cause of cancer-related death in that group. Physicians usually detect cancers by finding a lump in the prostate gland, which is a walnut shaped structure that helps to maintain the viability of sperm. Such lumps may be discovered during a routine checkup or an examination prompted by a patient's complaint of sudden urinary discomfort, or occasional impotence.

Prostate specific antigen (PSA) is one of the original molecular markers utilized for the diagnosis of prostate cancer. When an elevation of PSA is found in the serum, prostate cancer is likely (1). The ratio of free PSA/total PSA (f/t) can be used to diagnose prostate cancer more accurately in men whose PSA is elevated (2–4). If the f/t ratio is below 7% the likelihood is that the patient has cancer; if f/t is above 25%, no cancer is probably present.

Recently, another marker, prostate specific membrane antigen (PSAMA) has been introduced. PSMA is also of prognostic significance, with elevation correlating well with more advanced cancer (5).

It should be noted that use of these PSA molecular markers in evaluating men with possible prostate cancer still requires biopsy of the suspected mass for a definitive diagnosis. In light of the invasiveness of this procedure, less intrusive means for assessing patients for prostate cancer are actively being sought.

SUMMARY OF THE INVENTION

The present invention provides novel screening methods for use in combination with those currently available for the detection of prostate cancer. In accordance with the present invention, it has been discovered that the presence of certain ApoE genotypes can be correlated with an enhanced predisposition to prostate cancer. Among the three ApoE alleles, the E4 allele confers the highest disease risk. The E3 allele is associated with a lesser risk, and the E2 allele appears to be protective. Homozygosity at the E4 allele confers the highest risk of all. One embodiment of the present invention entails the determination of apoE genotype for assessing prostate cancer prognosis in patients at risk.

In a preferred embodiment, genotyping is performed employing apolipoprotein E oligonucleotide primers and polymerase chain reaction followed by allele specific oligonucleotide hybridization of amplified DNA products. Immunological assays are also simultaneously employed to assess prostate specific antigen levels in the biological fluids isolated from the patient In an alternative embodiment, apolipoprotein E genotyping is performed in conjunction with polymerase chain reaction employing a set of primers for amplifying prostate specific antigen nucleic acids. Another parameter of PSA levels, the ratio of free PSA to total PSA in blood of a patient would also be determined, a ratio below 7% indicating a propensity to or the presence of prostate cancer.

Another aspect of the invention is a method for assessing predisposition to prostate cancer in a patient comprising polymerase chain reaction assays amplifying known prostate cancer marker encoding-nucleic acids. The sample would be divided into multiple aliquots and specific primer pairs added to each aliquot, the primer pairs being specific for a predetermined prostate cancer marker selected from the group consisting of apolipoprotein E, PSA, PSAMA, basic fibroblast growth factor (bFGF), type IV collagenase, multidrug-resistance type I (mdr-1) protein, interleukin-1 β (il-1β), and interleukin-6 (il-6). The presence of elevated levels in the markers in the blood is indicative of a predisposition toward prostate cancer.

In yet another embodiment, methods are provided for assessing predisposition to prostate cancer in a patient which comprise obtaining a biological sample from the patient, determining the patient's ApoE genotype, determining biological levels of proteins in the sample, the proteins being selected from the group consisting of PSA, PSAMA, basic fibroblast growth factor (bFGF), type IV collagenase, multidrug-resistance type I (mdr-1) protein, interleukin-1β (il-1β), and interleukin-6 (il-6) and determining probability of prostate cancer by linear regression analysis wherein the presence or absence of prostate cancer is a dependent variable and independent variables are selected from the group consisting of ApoE genotype, PSA, PSAMA, basic fibroblast growth factor (bFGF), type IV collagenase, multidrug-resistance type I (mdr-1) protein, interleukin-1β (il-1β), and interleukin-6 (il-6).

DESCRIPTION OF THE INVENTION

Methods for diagnosing patients at risk for developing prostate cancer according to the invention, using genetic testing in conjunction with immunological assays for a series of markers associated with the occurrence of prostate cancer, are described hereinbelow.

Methods for detecting a new molecular marker for prostate cancer, the apolipoprotein E (ApoE) alleles, which are now used in the diagnosis of Alzheimer's disease (11) are utilized in the practice of the methods of the invention. The methods also entail the simultaneous detection and evaluation of PSA, PSMA, Il-6, bFGF, mdr-1 and collagenase. Elevated levels of these proteins have been shown to be associated with prostate cancer.

Apolipoprotein E (ApoE) performs various functions as a protein constituent of plasma lipoproteins, including its role in cholesterol metabolism. ApoE was first identified as a constituent of liver-synthesized very low density lipoproteins which function in the transport of triglycerides from the liver to peripheral tissues. There are three major isoforms of ApoE, referred to as ApoE2, ApoE3 and ApoE4 which are products of three alleles at a single gene locus. Three homozygous phenotypes (Apo-E2/2, E3/3 and E4/4) and three heterozygous phenotypes (ApoE2/3, ApoE4/3 and ApoE4/2) arise from the expression of any two of the three alleles. The most common phenotype is ApoE3/3 and the most common allele is E3 (12).

Apolipoprotein E is associated with the development of Alzheimer's disease. Among the three ApoE alleles, the E4 allele confers the highest risk for developing Alzheimer's disease. The E3 allele is associated with lesser risk, and the E2 allele appears to be protective. The E4-E4 genotype (i.e. two E4 alleles) confers the highest risk of all (11).

The antioxidant activity of certain ApoE alleles protects cells in culture from oxidative damage. The E2 allele is most protective, the E3 allele less so, and the E4 allele least protective of all (13). The decreased antioxidant activity of E4 may contribute to its association with Alzheimer's disease. Since antioxidants also protect against cancer (14), the expression of the E4 allele might predispose to the development of malignant disease.

Epidemiological data indicate that Alzheimer's disease and prostate cancer share a common incidence pattern. Onset of Alzheimer's disease before age 60 is infrequent and often due to specific gene abnormalities (15). Prostate cancer is also rare in men before age 60, and there is generally a strong genetic component in these cases. As men get older, the incidence of prostate cancer continues to increase, and cases with older onset do not generally have a family history (16,17). Like Alzheimer's disease, the supposition is that if men get old enough, most will develop prostate cancer.

Reverse transcriptase polymerase chain reaction would be utilized to isolate PSA encoding mRNA from mononuclear blood preparations from patients at risk. The presence of PSA mRNA in mononuclear cell preparations from whole blood suggests the presence of prostate cancer and thus is also an important biological marker for malignant disease.

Aberrant levels of certain proteins in the blood have also been correlated with the presence of prostate cancer. The methods of the invention entail the detection of protein levels of these candidate proteins to assess a patient's likelihood of developing prostate cancer. For example, prostate specific antigen (PSA) levels in the blood would be assessed using immunological assays on biological samples. Normal PSA levels are typically below 4.0 ng/ml. PSA levels will be assessed in a variety of ways. The free to total levels of PSA in the blood would be assessed. Prostate specific antigen density would also be assessed for predicting prostate cancer (23). Recent studies have revealed that prostate cancer is significantly associated with lower free PSA level and higher PSA density (23). Prostate specific membrane antigen levels in the blood of patients at risk would also be determined.

Aberrant levels of certain growth factors and cytokines have been associated with the incidence and metastatic potential of prostate cancer. Such protein molecules include interleukin I beta, interleukin 6 (22), basic fibroblastic growth factor (25), 72 kd and 92 kd type IV collagenase and mdr-1 drug resistance protein. The methods of the invention include simultaneous immunological assays of these proteins in biological samples of the patients being assessed.

The normal levels of these proteins in the blood of human subjects are provided in the prior art. However, immunological testing on control group subjects would readily provide this information for the normal population. Once the negative control information had been obtained, patients suspected of having, or at risk for the occurrence of prostate cancer would be assessed for the various parameters described above. The probability of prostate cancer would then be assessed by performing computerized logistic regression. The presence or absence of prostate cancer would be utilized as the dependent variable, whereas the independent variables would be stage of disease, apolipoprotein E genotype, PSA, PSAMA, basic fibroblast growth factor, type IV collagenase, and mdr-1 protein level. The analysis provides the coefficients of the factor "z" as described below. To calculate the probability that a man has prostate cancer, the coefficients of the "z" equation are used with the man's individual values of apolipoprotein E genotype, PSA, PSAMA, basic fibroblast growth factor, type IV collagenase, and mdr-1 protein level. In either case, once the "z" value is calculated, this value is introduced into the logistic model equation which is used for calculating the probability of prostate cancer, P(pc):

$P(pc)=1/(1+e^{-Z})$, where e is equal to 2.718 . . . , the base of the natural logarithms and where Z is determined by logistic regression (24). Another method, other than logistic regression, is a neural network. A neural network, such as that described in Neural Connection 1.0 Users Guide. SPSS, Inc, Chicago, Ill. 1995, may be used to calculate P(pc).

It should be noted that nucleic acid molecules encoding the foregoing proteins may also be quantitated from metastatic prostate cells in mononuclear blood preparations using hybridization techniques or polymerase chain reaction techniques.

The following examples are provided to illustrate certain embodiments of the invention. They are not intended to limit the invention in any way. The following protocols facilitate the practice of the present invention.

Sample Isolation

Peripheral blood mononuclear cells (PBMC) used as a source of DNA were purified from the blood of patients with prostate cancer by separation over a Ficoll-Hypaque gradient (Pharmacia, Piscataway, N.J.). Briefly, heparinized blood was diluted 1:3 with phosphate buffered saline, pH 7.4, and the solution layered onto Ficoll-Hypaque in a conical tube. Gradients were spun 45 minutes at 800×g and the PBMCs collected.

Polymerase Chain Reaction

Polymerase chain reactions are carried out in accordance with known techniques. See *Current Protocols in Molecular Biology.* (1996) eds. Ausubel, F. M. et al., John Wiley & Sons, NY. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product, the probe carrying a detectable label, and then detecting the label in accordance with known techniques, or by direct visualization on a gel. When PCR conditions allow for amplification of all ApoE allelic types, the types can be distinguished by hybridization with allelic specific probes, by restriction endonuclease digestion, by electrophoresis on denaturing gradient gels, or other techniques. A PCR protocol for determining the ApoE genotype has been previously described (15,18). Also see U.S. Pat. No. 5,508,167, the disclosure of which is incorporated by reference herein.

Methods for detecting other prostate cancer markers, such as PSA (3), free/total PSA ratio (3), PSA mRNA (6–8), basic fibroblast growth factor (bFGF) (25), type IV collagenase, multi-drug-resistance type I (mdr-1) (9), interleukin-1β (il-1β), interleukin-6 (il-6) (10, 22) have been described. Levels of these markers may be readily determined genetically or immunologically using standard techniques in molecular biology (i.e., nucleic acid hybridization) or by antibody/antigen based methods such as ELISA. Persons skilled in the art are familiar with such assay methods.

EXAMPLE 1

ApoE genotype in a group of men with prostate cancer was determined by polymerase chain reaction (PCR) followed by allele specific oligonucleotide hybridization (ASO) with standard probes for the three ApoE alleles, as has been described (15,18). ApoE phenotype can also be determined by immunohistochemical methods (19, 20). Persons skilled in the art would be able to use these and other methods for determining ApoE genotype.

Results

In 35 men with prostate cancer who were tested, the E4 allele was detected with a frequency of 24%. This frequency may be compared with an E4 allele frequency of 12% in the general male population (19). The high frequency of the E4 allele in the prostate cancer cases resembles its high frequency in Alzheimer's disease.

Furthermore, the two prostate cancer patients who were homozygous at the E4 alleles were age 52 and age 58, significantly younger than the average age (67+5.7 years, mean+SD) of the 33 other patients (p=0.0248, Mann Whitney U—Wilcoxon Rank Sum W test corrected for ties). In Alzheimer's disease, the patients who are homozygous E4-E4 also have the earliest disease onset (21).

The methods entail the simultaneous assessment of ApoE genotype combined with assessment of PSA levels. Free/total PSA ratio would be also determined. The presence of PSA mRNA in buffy coat samples would be assessed by amplification via polymerase chain reaction (6–8). The presence of PSA mRNA in buffy coat samples provides an indication that a primary prostate tumor may be present. Other prostate cancer markers include basic fibroblast growth factor (bFGF) (25), type IV collagenase, multi-drug-resistance type I (mdr-1) mRNA and/or protein (9), interleukin-1β (il-1β), interleukin-6 (il-6) (10). The presence or absence and levels of these markers would also be determined. The results of these tests would be combined with the results of the ApoE genotyping. Computerized logistic regression analysis will then be performed to determine the probability that prostate cancer was present.

For example, if a patient had a PSA of less than 5 ng/ml, a free/total PSA ratio above 25%, and the E2-E2 genotype, the probability of prostate cancer would be low. But if a patient had a PSA of more than 10 ng/ml, a free/total PSA ratio below 7%, and the E4-E4 genotype, the probability of prostate cancer would be high.

In another aspect, the present invention may also be used to advantage to predict individual susceptibility to prostate cancer, to stage prostate cancer, and to predict prognosis.

References

1. Murphy G P, Barren R J, Erickson S J, Bowes V A, Wolfert R L, Bartsch G, Klocker H, Pointner J, Reissigl A, McLeod D G, Douglas T, Morgan T, Kenny G M, Ragde H, Boynton A L, Holmes E H. Evaluation and comparison of two new prostate carcinoma markers. Free-prostate specific antigen and prostate specific membrane antigen. Cancer 1996;78:809–818.
2. Chen Y T, Luderer A A, Thiel R P, Carlson G, Cuny C L, Soriano T F. Using proportions of free to total prostate-specific antigen, age, and total prostate-specific antigen to predict the probability of prostate cancer. Urology 1996;47:518–524.
3. Luderer A A, Chen Y T, Soriano T F, Kramp W J, Carlson G, Cuny C, Sharp T, Smith W, Petteway J, Brawer M K, et al. Measurement of the proportion of free to total prostate-specific antigen improves diagnostic performance of prostate-specific antigen in the diagnostic gray zone of total prostate-specific antigen. Urology 1995;46:187–194.
4. Catalona W J, Smith D S, Wolfert R L, Wang T J, Rittenhouse H G, Ratliff T L, Nadler R B. Evaluation of percentage of free serum prostate-specific antigen to improve specificity of prostate cancer screening. JAMA 1995;274:1214–1220.
5. Murphy G, Ragde H, Kenny G, Barren R, Erickson S, Tjoa B, Boynton A, Holmes E, Gilbaugh J, Douglas T. Comparison of prostate specific membrane antigen, and prostate specific antigen levels in prostatic cancer patients. Anticancer Res 1995;15:1473–1479.
6. Sokoloff M H, Tso C-L, Kaboo R, Nelson S, Ko J, Dorey F, Figlin R A, Pang S, deKernion J, Belldegrun A. Quantitative polymerase chain reaction does not improve preoperative prostate cancer staging: a clinicopathological molecular analysis of 121 patients. Journal of Urology 1996;156:1560–1566.
7. Lehrer S. Use of the reverse transcriptase polymerase chain reaction for prostate specific antigen (PSA RT-PCR) as a molecular marker for prostate cancer. Journal of Urology 1997;in press:
8. Buttyan R, Katz A E, Olsson C A, Raffo A. Method for enhancing prostate-specific antigen detection—provides sensitive means to identify early stages of prostate cancer. U.S. patent application 1995; WPI Acc No:95–373812/48.
9. Greene G F, Kitadai Y, Pettaway C A, von Eschenbach A C, Bucana C D, Fidler I J. Correlation of metastasis-related gene expression with metastatic potential in human prostate carcinoma cells implanted in nude mice using an in situ messenger RNA hybridization technique. Am J Pathol 1997;150:1571–1582.
10. Degeorges A, Tatoud R, Fauvel Lafeve F, Podgorniak M P, Millot G, de Cremoux P, Calvo F. Stromal cells from human benign prostate hyperplasia produce a growth-inhibitory factor for LNCaP prostate cancer cells, identified as interleukin-6. Int J Cancer 1996;68:207–214.
11. Saunders A M, Hulette O, Welsh Bohmer K A, Schmechel D E, Crain B, Burke J R, Alberts M J, Strittmatter W J, Breitner J C, Rosenberg C, Scott S V, Gaskell P C J, Pericak Vance M A, Roses A D. Specificity, sensitivity, and predictive value of apolipoprotein-E genotyping for sporadic Alzheimer's disease. Lancet 1996;348:90–93.
12. Mahley R W. Apolipoprotein E: Cholesterol transporting protein with expanding role in cell biology. Science 1988;240:622–630.
13. Miyata M, Smith J D. Apolipoprotein E allele-specific antioxidant activity and effects on cytotoxicity by oxidative insults and β-amyloid peptides. Nature Genetics 1996;14(1):55–61.
14. Duthie S J, Ma A, Ross M A, Collins A R. Antioxidant supplementation decreases oxidative DNA damage in human lymphocytes. Cancer Res 1996;56:1291–1295.
15. Corder E H, Saunders A M, Strittmatter W J, Schmechel D E, Gaskell P C, Small G W, Roses A D, Haines J L, Pericak Vance M A. Gene dose of apolipoprotein E type 4 allele and the risk of Alzheimer's disease in late onset families. Science 1993;261:921–923.
16. Eastman P. Search for prostate cancer gene sites may succeed in 1996. J Natl Cancer Inst 1996;88:952–953.
17. Stephenson J. Prostate cancer gene hunters track their quarry. JAMA 1996;276(11):861–863.
18. Wenham P R, Price W H, Blundell G. Apolipoprotein E genotyping by one-stage PCR. Lancet 1991;337:1158–1159.
19. Poirier J, Davignon J, Bouthillier D, Kogan S, Bertrand P, Gauthier S. Apolipoprotein E polymorphism and Alzheimer's disease. Lancet 1993;342:697–699.
20. Bouthillier D, Sing C F, Davignon J. Apolipoprotein E phenotyping with a single method: application to the study of informative mating. J Lipid Res 1983;24:1060–1069.
21. Blacker D, Haines J L, Rodes L, Terwedow H, Go R C P, Harrell L E, Perry R T, Bassett S S, Chase G, Meyers D, Albert M S, Tanzi R. ApoE-4 and age at onset of Alzheimer's disease: the NIMH genetics initiative. Neurology 1997;48:139–147.
22. Twillie, D. A. et al., Interleukin-6: a candidate mediator of human prostate cancer morbidity. Urology 1995; 45:542–9.
23. Catalona, W., et al. Serum free prostate specific antigen and prostate specific antigen density measurements for predicting cancer in men with prior negative prostatic biopsies. J. Urology 1997 158:2162–2187.
24. Lehrer, S., et al., Nomograms for determining the probability of axillary node involvement in women with breast cancer. J. Cancer Res. Clin. Oncol. 1995 121:123–125
25. Meyer, C. E. et al., Serum basic fibroblast growth factor in men with and without prostate cancer. Cancer 1995 76:2304–2311.

While certain embodiments of the present invention have been described and exemplified above as preferred embodiments, the invention is not limited to those embodiments, but is capable of variation and modification within the scope of the appended claims

What is claimed:

1. A method for screening for prostate cancer in a patient comprising genotyping said patient at apolipoprotein E alleles, a genotype of ApoE4/ApoE4 indicating an increased propensity for prostate cancer.

2. A method as claimed in claim 1, wherein said genotyping is performed employing apolipoprotein E oligonucleotide primers and polymerase chain reaction followed by allele specific oligonucleotide hybridization of amplified DNA products.

3. A method as claimed in claim 1, further comprising an immunological assay for the presence of prostate specific antigen in the blood of said patient.

4. A method as claimed in claim 1, wherein said apolipoprotein E genotyping is performed in conjunction with polymerase chain reaction employing a set of primers for amplifying prostate specific antigen nucleic acids.

5. A method as claimed in claim 1, wherein a ratio of free PSA to total PSA in blood of said patient is also determined, a ratio below 7% indictating a propensity to or the presence of prostate cancer.

6. A method for screening for prostate cancer in a patient comprising:

a) obtaining a biological sample from said patient;

b) determining said patient's ApoE genotype;

c) determining biological levels of at least on protein in said sample, said protein being selected from the group consisting of PSA, PSAMA, basic fibroblast growth factor (bFGF), type IV collagenase, multi-drug-resistance type I (mdr-1) protein, interleukin-1β (il-1β), and interleukin-6 (il-6); and d) determining probability of prostate cancer by linear regression analysis wherein the presence or absence of prostate cancer is a dependent variable and independent variables are selected from the group consisting of PSA, PSAMA, basic fibroblast growth factor (bFGF), type IV collagenase, multi-drug-resistance type I (mdr-1) protein, interleukin-1β (il-1β), and interleukin-6 (il-6).

7. A method as claimed in claim 6, wherein said DNA is obtained from buffy coat cells isolated from a blood sample.

* * * * *